US00PP32688P2

(12) United States Plant Patent
Barnes

(10) Patent No.: US PP32,688 P2
(45) Date of Patent: Dec. 22, 2020

(54) ***PETUNIA* PLANT NAMED 'BBTUN10102'**

(50) Latin Name: ***Petunia* X *hybrida***
Varietal Denomination: BBTUN10102

(71) Applicant: Brent D. Barnes, Riverside, CA (US)

(72) Inventor: Brent D. Barnes, Riverside, CA (US)

(73) Assignee: PLANT 2I LLC, Bonsall, CA (US)

( * ) Notice: Subject to any disclaimer, the term of this patent is extended or adjusted under 35 U.S.C. 154(b) by 0 days.

(21) Appl. No.: 16/873,354

(22) Filed: Mar. 26, 2020

(51) Int. Cl.
*A01H 5/02* (2018.01)
*A01H 6/82* (2018.01)

(52) U.S. Cl.
USPC ..... Plt./356.2
CPC ..... *A01H 6/824* (2018.05)

(58) Field of Classification Search
USPC ..... Plt./356.2
CPC ..... A01H 5/02
See application file for complete search history.

*Primary Examiner* — Kent L Bell
(74) *Attorney, Agent, or Firm* — C. A. Whealy

(57) ABSTRACT

A new and distinct *Petunia* plant named 'BBTUN10102', characterized by its upright to outwardly spreading and mounding to eventually trailing plant habit; vigorous growth habit and rapid growth rate; freely branching habit; dense and bushy plant form; early and freely flowering habit; dark purple-colored velvety flowers; and excellent garden performance.

2 Drawing Sheets

Figure 1:
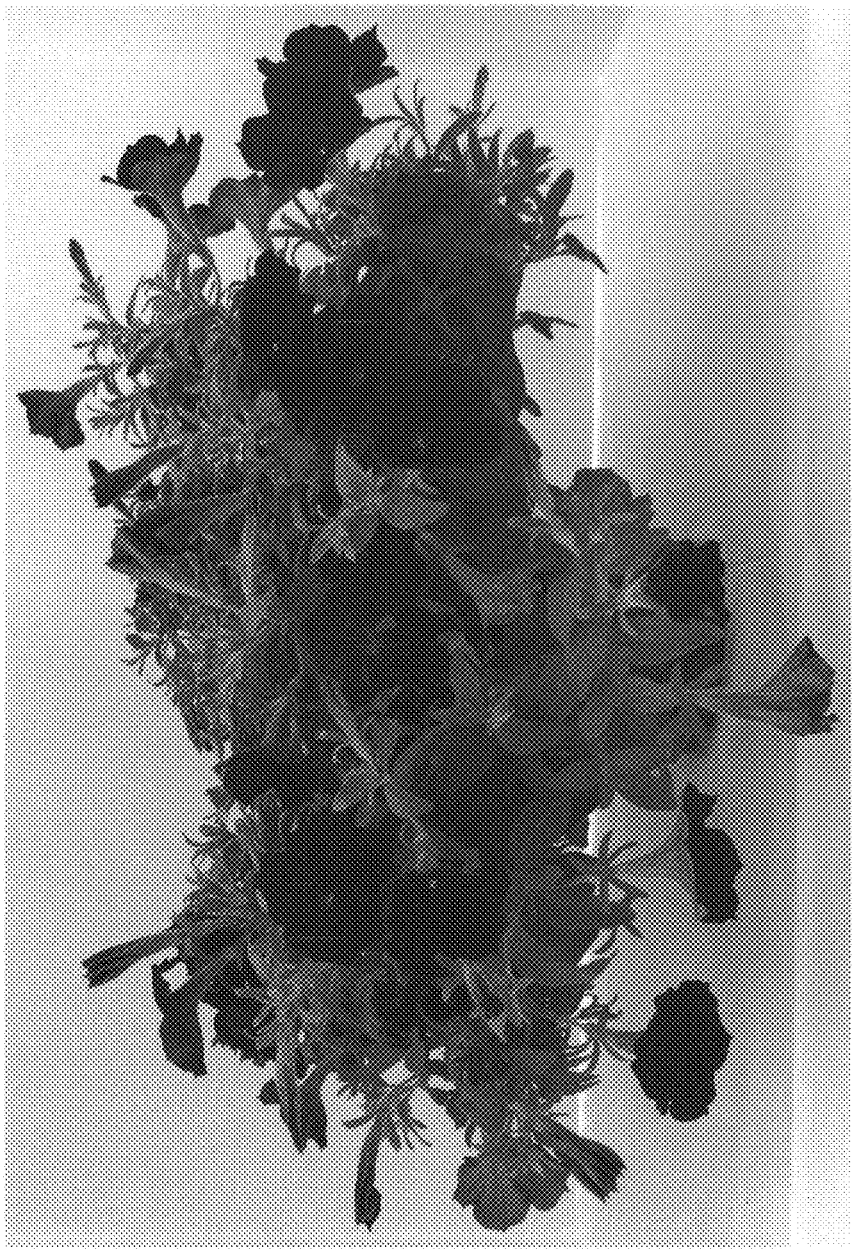

Botanical designation: *Petunia* X *hybrida*.
Cultivar denomination: 'BBTUN10102'.

BACKGROUND OF THE INVENTION

The present invention relates to a new and distinct cultivar of *Petunia* plant, botanically known as *Petunia* X *hybrida* and hereinafter referred to by the name 'BBTUN10102'.

The new *Petunia* plant is a product of a planned breeding program conducted by the Inventor in Bonsall, Calif. The objective of the breeding program is to create new vigorous, freely-branching and uniformly mounding *Petunia* plants with early and freely flowering habit, unique attractive flowers and good garden performance.

The new *Petunia* plant originated from a cross-pollination made by the Inventor on Aug. 17, 2016 in Bonsall, Calif. of a proprietary seedling selection of *Petunia* X *hybrida* identified as code number 15P857-01, not patented, as the female, or seed, parent with a proprietary seedling selection of *Petunia* X *hybrida* identified as code number 15PB514-03, not patented, as the male, or pollen, parent. The new *Petunia* plant was discovered and selected by the Inventor as a single flowering plant within the progeny of the stated cross-pollination in a controlled greenhouse environment in Bonsall, Calif. on Sep. 19, 2017.

Asexual reproduction of the new *Petunia* plant by vegetative terminal cuttings in a controlled greenhouse environment in Bonsall, Calif. since Sep. 22, 2017 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBTUN10102'. These characteristics in combination distinguish 'BBTUN10102' as a new and distinct *Petunia* plant:

1. Upright to outwardly spreading and mounding to eventually trailing plant habit.
2. Vigorous growth habit and rapid growth rate.
3. Freely branching habit; dense and bushy plant form.
4. Early and freely flowering habit.
5. Dark purple-colored velvety flowers.
6. Excellent garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more vigorous and larger than plants of the female parent selection.
2. Plants of the new *Petunia* are denser and bushier than plants of the female parent selection.
3. Plants of the new *Petunia* have larger flowers than plants of the female parent selection.
4. Plants of the new *Petunia* perform better in the garden than plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more vigorous than plants of the male parent selection.
2. Plants of the new *Petunia* are more outwardly spreading than and not as upright as plants of the male parent selection.

3. Plants of the new *Petunia* are more freely branching and denser and bushier than plants bf the male parent selection.
4. Plants of the new *Petunia* perform better in the garden than plants of the male parent selection.

Plants of the new *Petunia* can be compared to plants of 'USTUNI6001', disclosed in U.S. Plant Pat. No. 17,730. In side-by-side comparisons, plants of the new *Petunia* differ primarily from plants of 'USTUNI6001' in the following characteristics:

1. Plants of the new *Petunia* are more vigorous than plants of 'USTUNI6001'.
2. Plants of the new *Petunia* are more outwardly spreading than and not as upright as plants of 'USTUNI6001'.
3. Plants of the new *Petunia* are denser and bushier than plants of 'USTUNI6001'.
4. Plants of the new *Petunia* and 'USTUNI6001' differ in flower color as plants of the new *Petunia* have dark purple-colored flowers whereas plants of 'USTUNI6001' have bright pink-colored flowers.
5. Plants of the new *Petunia* perform better in the garden than plants of 'USTUNI6001'.

Plants of the new *Petunia* can be compared to plants of 'KL 1117', disclosed in U.S. Plant Pat. No. 25,485. In side-by-side comparisons, plants of the new *Petunia* differ primarily from plants of 'KL 1117' in the following characteristics:

1. Plants of the new *Petunia* are more vigorous and larger than plants of 'KL 1117'.
2. Plants of the new *Petunia* are more outwardly spreading than and not as upright as plants of 'KL 1117'.
3. Plants of the new *Petunia* are denser and bushier than plants of 'KL 1117'.
4. Plants of the new *Petunia* and 'KL 1117' differ in flower color as plants of the new *Petunia* have dark purple-colored flowers whereas plants of 'KL 1117' have white-colored flowers.
5. Plants of the new *Petunia* perform better in the garden than plants of 'KL 1117'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1 of 2) is a side perspective view of a typical flowering plant of 'BBTUN10102' grown in a container.

Figure 2:
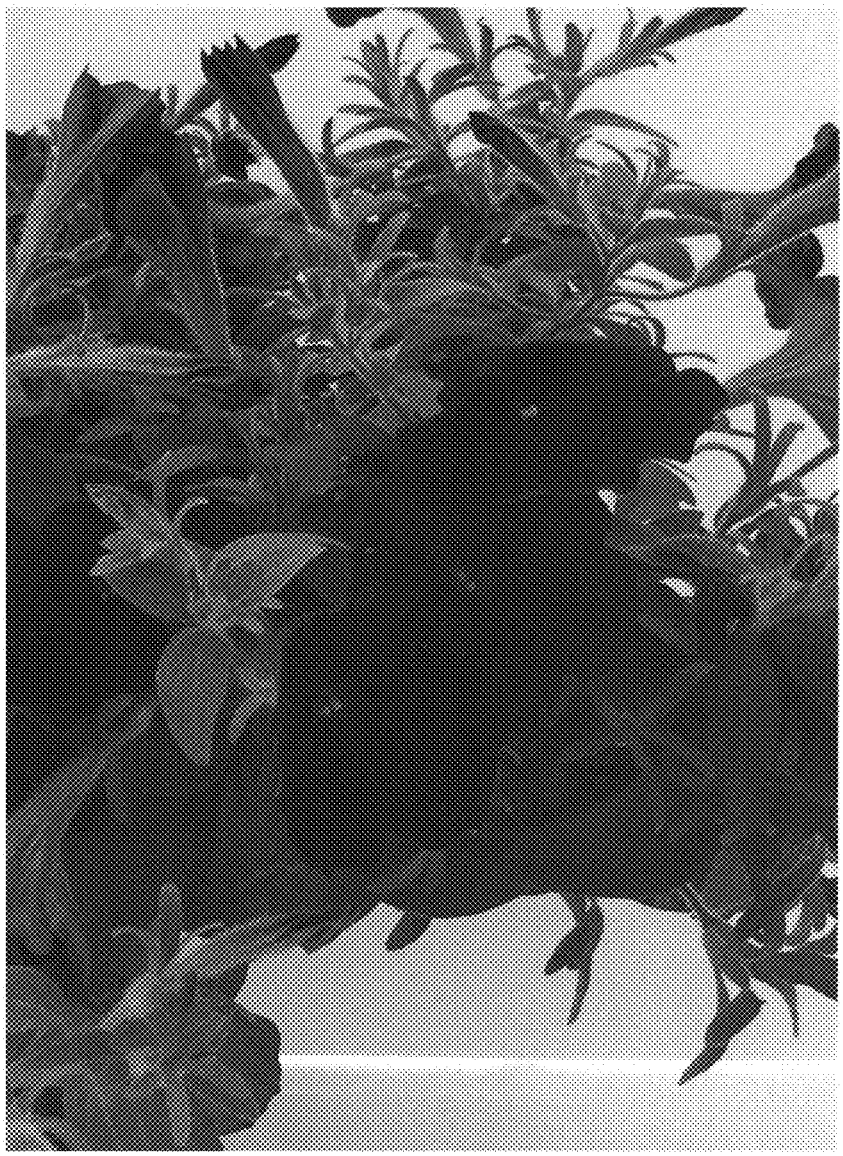

The photograph on the second sheet (FIG. 2 of 2) is a close-up view of a typical flowering plant of 'BBTUN10102'.

DETAILED BOTANICAL DESCRIPTION

The aforementioned photographs and following observations and measurements describe plants grown during the autumn and winter in 10.8-cm containers in a glass-covered greenhouse in Loudon New Hampshire and under cultural practices typical of commercial *Lobelia* production. During the production of the plants, day and night temperatures averaged 20° C. Plants were pinched three weeks after planting and were 14 weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'BBTUN10102'.

Parentage:

*Female, or seed, parent*.—Proprietary seedling selection of *Petunia* X *hybrida* identified as code number 15P857-01, not patented.

*Male, or pollen, parent*.—Proprietary seedling selection of *Petunia* X *hybrida* identified as code number 15PB514-03, not patented.

Propagation:

*Type*.—Terminal vegetative cuttings.

*Time to initiate roots, summer*.—About three to four days at ambient temperatures ranging from 17° C. to 29° C.

*Time to initiate roots, winter*.—About five to seven days at ambient temperatures ranging from 17° C. to 21° C.

*Time to produce a rooted plant, summer*.—About three weeks at ambient temperatures ranging from 17° C. to 29° C.

*Time to produce a rooted plant, winter*.—About four weeks at ambient temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; freely branching habit with lateral branches potentially developing at every node, dense and bushy plant form; pinching enhances development of lateral branches; vigorous growth habit and rapid growth rate.

*Plant height, soil level to top of foliar plane*.—About 12.5 cm.

*Plant height, soil level to top of floral plane*.—About 15 cm.

*Plant diameter* (*area of spread*).—About 40.5 cm.

*Lateral branches*.—Length: About 13.5 cm. Diameter: About 3 mm to 3.5 mm. Internode length: About 8 mm to 12 mm. Strength: Strong; flexible, not brittle. Aspect: Initially upright then outwardly spreading to almost horizontal and eventually trailing. Texture and luster: Densely pubescent; not viscid; moderately glossy. Color, developing: Close to 144A. Color, developed: Close to 144A.

Leaf description:

*Arrangement*.—Alternate before flowering; opposite after flowers develop; leaves simple.

*Length, largest leaves*.—About 4.2 cm to 4.5 cm.

*Width, largest leaves*.—About 2.75 cm to 3 cm.

*Shape*.—Mostly ovate.

*Apex*.—Acute.

*Base*.—Obtuse with cuneate tendencies.

*Margin*.—Entire, not undulate.

*Texture and luster, upper and lower surfaces*.—Pubescent; somewhat glossy.

*Venation pattern*.—Pinnate, arcuate.

*Color*.—Developing leaves, upper surface: Close to 146A. Developing leaves, lower surface: Close to 146B. Fully expanded leaves, upper surface: Close to 147A; venation, close to 146A. Fully expanded leaves, lower surface: Close to 147B; venation, close to 147A

*Petioles*.—Length: About 6 mm to 10 mm. Diameter: About 2 mm to 2.5 mm. Strength: Strong, flexible. Texture and luster, upper and lower surfaces: Pubescent; somewhat glossy. Color, upper surface: Close to 146A. Color, lower surface: Close to 146A to 146B.

Flower description:

*Flower type and flowering habit*.—Single terminal and axillary salverform flowers; flowers face mostly upward to outwardly; freely flowering habit with about 30 to 35 open flowers per plant at one time.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About five to seven days; flowers persistent.

*Fragrance*.—Faint; sweet, pleasant.

*Flower buds*.—Length, with sepals: About 1.5 cm. Diameter, with sepals: About 2 cm. Length, without sepals: About 1.1 cm. Diameter, without sepals: About 3 mm to 3.5 mm. Shape: Oblong, elongate. Texture and luster: Pubescent; somewhat glossy. Color, sepals: Close to 146A. Color, petals: Close to 144A.

*Flower diameter*.—About 4.25 cm to 4.75 cm.

*Flower depth (height)*.—About 3.6 cm to 4 cm.

*Throat diameter, distal*.—About 7.5 mm to 9 mm.

*Tube length*.—About 2.7 cm to 3 cm.

*Tube diameter, proximally*.—About 2 mm.

*Petals*.—Quantity and arrangement: Five petals fused in a single salverform whorl. Petal lobe length (from throat): About 1.8 cm to 2.2 cm. Petal lobe width: About 2 cm to 2.2 cm. Petal lobe shape: Spatulate. Petal lobe apex: Cuspidate. Petal lobe margin: Entire; slightly undulate. Petal lobe texture and luster, upper surface: Smooth, glabrous; velvety; slightly glossy. Petal lobe texture and luster, lower surface: Smooth, glabrous; moderately velvety; slightly glossy. Throat texture and luster: Smooth, glabrous; slightly glossy. Tube texture and luster: Densely pubescent; slightly glossy. Color: When opening, upper surface: Close to 83A. When opening, lower surface: Close to 83B. Fully opened, upper surface: Close to 83A; venation, close to 83A; color does not change with development. Fully opened, lower surface: Close to 83B; midvein, close to N79A; lateral venation, close to 83B; color becoming closer to 83D with development. Flower throat (inside): Close to 83A; venation, close to N79A. Flower tube (outside): Close to 83A to 83B; proximally, close to 144A to 144B; venation, close to 144A to 144B.

*Sepals*.—Quantity and arrangement: Five sepals fused in a single star-shaped whorl. Length: About 2 cm. Width: About 3.5 mm to 4 mm. Shape: Linear, outwardly arching. Apex: Acute. Margin: Entire. Texture and luster, upper and lower surfaces: Pubescent; somewhat glossy. Color: When opening, upper and lower surfaces: Close to 146A. Fully developed, upper surface: Close to 146A. Fully developed, lower surface: Slightly darker than 146A.

*Peduncles*.—Length: About 1.5 cm to 1.75 cm. Width: About 1.5 mm. Strength: Strong; wiry and flexible, not brittle. Angle: Upright to horizontal. Texture and luster: Pubescent; somewhat glossy. Color: Close to 144A.

*Reproductive organs*.—Stamens: Quantity per flower: Five. Filament length: About 2 cm. Filament color: Close to 145D. Anther size: About 0.75 mm by 1 mm. Anther shape: Bi-lobed. Anther color: Close to 4C to 4D. Pollen amount: None observed. Pistils: Quantity per flower: One. Pistil length: About 2 cm. Style length: About 1.7 cm. Style color: Close to 145D. Stigma diameter: About 1.5 mm. Stigma shape: Round. Stigma color: Close to 144A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1° C. to about 40° C.

It is claimed:

1. A new and distinct *Petunia* plant named 'BBTUN10102' as illustrated and described.

* * * * *